United States Patent [19]

Faustini et al.

[11] Patent Number: 4,771,043

[45] Date of Patent: Sep. 13, 1988

[54] STEROIDIC AROMATASE INHIBITORS

[75] Inventors: Franco Faustini; Roberto D'Alessio; Vittoria Villa; Enrico di Salle; Paolo Lombardi, all of Milan, Italy

[73] Assignee: Farmitalia Carlo Erba, S.p.A., Milan, Italy

[21] Appl. No.: 887,438

[22] Filed: Jul. 21, 1986

[30] Foreign Application Priority Data

Aug. 1, 1985 [GB] United Kingdom ............... 8519398

[51] Int. Cl.$^4$ .................... C07J 1/00; A61K 31/56
[52] U.S. Cl. ................................. 514/177; 260/397.3
[58] Field of Search .................... 260/397.3; 514/177

[56] References Cited

U.S. PATENT DOCUMENTS

| | | | |
|---|---|---|---|
| 3,014,932 | 12/1961 | Ringold et al. | 260/397.3 |
| 3,239,510 | 3/1966 | Sasaki | 260/397.3 |
| 3,320,291 | 5/1967 | Andreades et al. | 260/397.3 |
| 3,781,276 | 12/1973 | Shapiro | 260/397.3 |
| 4,028,348 | 6/1977 | Bíte et al. | 260/397.3 |

FOREIGN PATENT DOCUMENTS 1042291 11/1961 United Kingdom.
1022757 3/1966 United Kingdom.

OTHER PUBLICATIONS

Cancer Research (Suppl.) 42, 3327s–3333s (1982); Covey et al.
J.C.S. Chem. Comm. (1973), pp. 72–73; Herzog et al.

Primary Examiner—Leonard Schenkman
Assistant Examiner—Joseph A. Lipovsky
Attorney, Agent, or Firm—Murray & Whisenhunt

[57] ABSTRACT

The invention relates to 6-substituted androsta-1,4-diene-3,17-dione derivatives wherein the 6 substituent is an azido, amino or substituted amino group.

The invention provides also a process for preparing the said compounds and pharmaceutical compositions containing same.

The compounds of the invention are useful aromatase inhibitors and can be used, e.g., in the treatment of hormone-dependent tumors.

9 Claims, No Drawings

STEROIDIC AROMATASE INHIBITORS

The present invention relates to new 6-substituted androsta-1,4-diene-3,17-dione, to a process for their preparation and to pharmaceutical compositions containing them. The invention provides compounds of the following formula

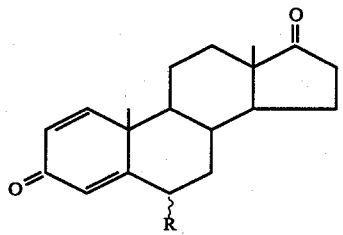
(I)

wherein R is
(1) the group -$N_3$ (azido group);
(2) a group

wherein each of $R_1$ and $R_2$ is, independently, hydrogen or unsubstituted $C_1$–$C_{22}$ alkyl;
(3) a group —$NHCOR_3$ wherein $R_3$ is
(a) hydrogen;
(b) $C_1$–$C_3$ alkoxy or carboxy;
(c) $C_1$–$C_{22}$ alkyl either unsubstituted or substituted by a carboxy group; or
(d) a group

wherein $R_1$ and $R_2$ are as defined above; or
(4) a group —$NHSO_2R_4$ wherein $R_4$ is unsubstituted $C_1$–$C_4$ alkyl, or phenyl either unsubstituted or substituted by $C_1$–$C_3$ alkyl, halogen or nitro.

The invention includes also the pharmaceutically acceptable salts of the compounds of formula (I), as well as all the possible isomers of formula (I), both separately and in mixture.

In the formulae of this specification a wavy line bond (~) indicates that a substituent may be either in the α-configuration (i.e. in equatorial position) or in the β-configuration (i.e. in axial position) or both.

Consequently, anywhere a formula has a substituent with a wavy line bond the formula may represent a compound having the substituent only in the α-configuration or only in the β-configuration or the formula may represent a mixture of both compounds having the substituent in the α-configuration and compounds having the substituent in the β-configuration. In the specification the alkyl groups as well as the aliphatic moieties of the alkoxy groups may be branched or straight chain.

An unsubstituted $C_1$–$C_{22}$ alkyl group is, preferably, a branched or straight chain $C_1$–$C_{17}$ alkyl group, in particular, for instance, methyl, ethyl, n-propyl, n-butyl, tert.butyl, n-pentyl, n-hexyl, n-heptyl, n-octyl, n-nonyl, n-decyl, n-undecyl, n-tridecyl, n-pentadecyl or n-heptadecyl.

A $C_1$–$C_3$ alkoxy group is, preferably, methoxy or ethoxy.

A $C_1$–$C_{22}$ alkyl substituted by carboxy is, preferably, a linear $C_1$–$C_4$ alkyl with a terminal carboxy group, for instance, carboxymethyl or 2-carboxyethyl.

A $C_1$–$C_3$ or $C_1$–$C_4$ alkyl group is, preferably, methyl or ethyl.

A halogen is, preferably, chlorine or bromine.

When R or $R_3$ is a group

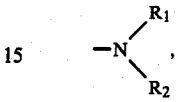

preferably each $R_1$ and $R_2$ is, independently, hydrogen or $C_1$–$C_4$ alkyl, in particular methyl or ethyl; particularly preferred groups

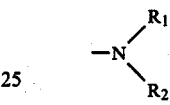

are amino for the R substituent, and amino, dimethylamino and diethylamino for the $R_3$ substituent.

When R is a group —$NHCOR_3$, preferably $R_3$ is (a') hydrogen; (b') $C_1$–$C_3$ alkoxy, in particular methoxy or ethoxy; or carboxy; (c') unsubstituted $C_1$–$C_{17}$ alkyl or $C_1$–$C_4$ alkyl substituted by carboxy.

Particularly preferred values of R, when R is —$NHCOR_3$, are formylamino, ethoxycarbonylamino, oxaloamino, acetylamino, propionylamino, butyrylamino, pivaloylamino, hexanoylamino, heptanoylamino, octanoylamino, decanoylamino, dodecanoylamino, tetradecanoylamino, hexadecanoylamino, octadecanoylamino and 3-carboxypropionylamino.

When R is a group —$NHSO_2R_4$, preferably $R_4$ is unsubstituted $C_1$–$C_4$ alkyl, in particular methyl or ethyl, or phenyl either unsubstituted or substituted by $C_1$–$C_3$ alkyl, in particular methyl, or by nitro.

Particularly preferred values of R, when R is —$NHSO_2R_4$, are methanesulfonylamino, ethanesulfonylamino and p-toluenesulfonylamino.

As already said, the invention includes also the pharmaceutically acceptable salts of the compounds of formula (I).

Preferred salts according to the invention are the salts of the compounds of formula (I) wherein R is a group

as defined above with pharmaceutically acceptable acids, both inorganic acids such as, e.g., hydrochloric, sulfuric or phosphoric acid, and organic acids such as, e.g., citric, fumaric, maleic, malic, ascorbic, succinic, tartaric, benzoic, acetic, phenylacetic, cyclohexylacetic, 3-cyclohexylpropionic, methanesulfonic, ethanesulfonic, benzenesulfonic, p-toluenesulfonic or p-nitrobenzenesulfonic acid.

Also the quaternary ammonium salts and hydroxides of the compounds of formula (I) wherein R is

are within the scope of the invention: they are, for instance, quaternary alkyl, e.g., methyl, ethyl or cetyl, ammonium salts, e.g. iodides, bromides or chlorides, or hydroxides. Though the above indicated salts are the preferred ones according to the invention, nevertheless this is meant to include also the pharmaceutically acceptable salts of the compounds of formula (I) containing an acidic, i.e. carboxy, group, with pharmaceutically acceptable bases. These may be both inorganic bases such as, for instance, alkali metal, e.g. sodium or potassium, or alkaline earth metal, e.g. calcium or magnesium, hydroxides, and organic bases such as, for instance, alkyl amines, e.g. methylamine or triethylamine, aralkylamines, e.g. benzylamine, dibenzylamine, α- or β-phenyl-ethylamine, or heterocyclic amines such as, e.g., piperidine, 1-methyl-piperidine, piperazine or morpholine. A preferred class of compounds according to the invention are the compounds of formula (I) wherein R is (1) —$N_3$;
(2) a group

wherein each of $R_1$ and $R_2$ is, independently, hydrogen or $C_1$–$C_4$ alkyl;
(3) a group —$NHCOR_3$, wherein $R_3$ is (a') hydrogen; (b') $C_1$–$C_3$ alkoxy or carboxy; (c') unsubstituted $C_1$–$C_{17}$ alkyl or $C_1$–$C_4$ alkyl substituted by carboxy; or
(4) a group —$NHSO_2R_4$, wherein $R_4$ is unsubstituted $C_1$–$C_4$ alkyl, or phenyl either unsubstituted or substituted by $C_1$–$C_3$ alkyl, and the pharmaceutically acceptable salts thereof.

In the above preferred class a $C_1$–$C_4$ alkyl is, preferably, methyl or ethyl, a $C_1$–$C_3$ alkoxy is, preferably, methoxy or ethoxy; an unsubstituted $C_1$–$C_{17}$ alkyl is, preferably, methyl, ethyl, n-propyl, n-hexyl or n-undecyl; a $C_1$–$C_4$ alkyl substituted by carboxy is, preferably, 2-carboxyethyl; a phenyl group substituted by $C_1$–$C_3$ alkyl is, preferably, p-tolyl.

The compounds of the present invention are optically active compounds and the stereochemistry of the ring-junctions is the same as that of the natural androstane series.

Examples of specific compounds preferred under the invention are the following compounds, both as pure 6α- or 6β-epimers and as 6(α,β) mixture of 6α- and 6β-epimers:

6-azido androsta-1,4-diene-3,17-dione;
6-amino androsta-1,4-diene-3,17-dione;
6-methylamino androsta-1,4-diene-3,17-dione;
6-(N',N'-dimethylcarbamido)-androsta-1,4-diene-3,17-dione;
6-ethylamino androsta-1,4-diene-3,17-dione;
6-(N',N'-diethylcarbamido)-androsta-1,4-diene-3,17-dione;
6-formylamino androsta-1,4-diene-3,17-dione;
6-ethoxycarbonylamino androsta-1,4-diene-3,17-dione;
6-oxaloamino androsta-1,4-diene-3,17-dione;
6-acetylamino androsta-1,4-diene-3,17-dione;
6-propionylamino androsta-1,4-diene-3,17-dione;
6-methanesulfonylamino androsta-1,4-diene-3,17-dione;
6-(p-toluenesulfonyl)amino androsta-1,4-diene-3,17-dione, and the pharmaceutically acceptable salts of the compounds containing a salifiable group.

The compounds of the invention may be prepared by a process comprising:
(A) reacting a compound of formula (II)

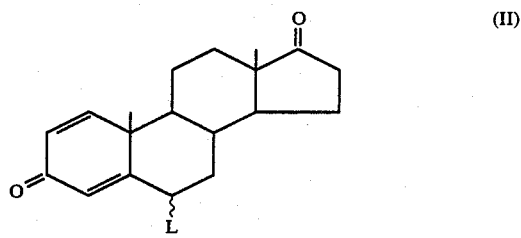

wherein
L is a leaving group displaceable by nucleophilic substitution, with a compound of formula (III)

wherein
M is an alkali metal or ammonium cation or a trialkylsilyl group, so obtaining a compound of formula (I) wherein R is the group —$N_3$; or
(B) reducing a compound of formula (I) wherein R is the group —$N_3$ so obtaining a compound of formula (I) wherein R is a group

wherein, depending upon the reaction conditions, $R_1$ and $R_2$ are both hydrogen or one of $R_1$ and $R_2$ is hydrogen and the other is unsubstituted $C_1$–$C_{22}$ alkyl; or
(C) alkylating a compound of formula (I) wherein R is a group

wherein $R_1$ and $R_2$ are both hydrogen, so obtaining a compound of formula (I) wherein at least one of $R_1$ and $R_2$ is unsubstituted $C_1$–$C_{22}$ alkyl; or
(D) acylating a compound of formula (I) wherein R is a group

wherein $R_1$ and $R_2$ are both hydrogen, with an acylating agent carrying a —$COR_3$ or $SO_2R_4$ moiety, wherein R₃ and R₄ are as defined above, so obtaining a compound of formula (I) wherein R is a group —NHCOR₃ or, respectively, a group —NHSO₂R₄, wherein R₃ and R₄ are as defined above [in the context of D), acylating includes sulphonating];

and, if desired, salifying a compound of formula (I) or obtaining a free compound of formula (I) from a salt thereof and/or, if desired, separating a mixture of isomers of formula (I) into the signal isomers.

In the compounds of formula (II) the leaving group L may be a halogen atom or a residue of a reactive ester, either sulfonic acid ester or carboxylic acid ester, of an alcohol. When L is halogen, iodine, bromine and chlorine are preferred.

When L is an ester residue as defined above, it is, preferably, a group R₅SO₂—O— wherein R₅ is an optionally halo-substituted C₁-C₄ alkyl, in particular methyl or trifluoromethyl, or phenyl optionally substituted by C₁-C₄ alkyl or nitro, in particular p-tolyl or p-nitrophenyl, or a group R₆—COO— wherein R₆ has the same meanings reported above for R₅, being, preferably, methyl, trifluoromethyl, or p-nitrophenyl.

When M in the compound of formula (III) is an alkali metal cation, this is, preferably, a sodium or lithium cation.

When M is a trialkylsilyl group, it is, preferably, a trimethylsilyl, triethylsilyl or dimethyltert-butylsilyl group. Accordingly, preferred compounds of formula (III) are sodium azide, lithium azide, trimethylsilylazide, triethylsilylazide, dimethyltert-butylsilylazide and, furthermore, ammonium azide.

The reaction between a compound of formula (II) and a compound of formula (III) is preferably carried out in an organic solvent such as, for instance, N,N-dimethylformamide, N,N-dimethylacetamide or dimethylsulfoxide; some water or an alcoholic, e.g. methanolic or ethanolic, aqueous solution may be added, if desired, to increase the solubility of the alkali metal azide of formula (III) in the reaction medium. The reaction may be performed at any temperature from about room temperature to the boiling point of the solvent used, and the reaction time may vary from some minutes to several hours.

The reduction of a compound of formula (I) wherein R is the group —N₃ in order to obtain a compound of formula (I) wherein R is a group

wherein R₁ and R₂ are both hydrogen, may be carried out by known methods, by a variety of reducing agents such as, for example, propane-1,3-dithiol/triethylamine [according to the method of Hagan Bayley et al, Tetr. Lett. 39, 3633 (1978)], or dithiothreitol in aqueous solution, or mercaptoacetic acid/triethylamine, or triphenylphosphine in aqueous solution [according to, e.g., the method of N. Knouzi et al. Bull. Soc. Chim. Fr. 1985, 815] or operating by catalytic reduction, for instance with H₂/Pd or H₂/Lindlar catalyst in an organic solvent, for example in alcoholic medium, e.g. methanol or ethanol, at a temperature from, e.g., the room temperature to about 100° C., and for reaction times which may vary from about some minutes to several hours.

The reduction of a compound of formula (I) wherein R is the group N₃ in order to obtain a compound of formula (I) wherein R is a group

wherein one of R₁ and R₂ is hydrogen and the other is unsubstituted C₁-C₂₂ alkyl may be performed, e.g., by reaction with a tri-C₁-C₂₂-alkyl-borane, e.g., tri-methyl- or tri-ethyl-borane, preferably operating in an inert organic solvent such as, for instance, benzene, toluene, xylene or n-hexane, at a temperature which may vary between the room temperature and the boiling point of the solvent.

The alkylation of a compound of formula (I) wherein R is a group

wherein R₁ and R₂ are both hydrogen to obtain a corresponding compound of formula (I) wherein at least one of R₁ and R₂ is a C₁-C₂₂ alkyl group may be carried out by reaction with a suitable alkylating agent which may be, e.g., a C₁-C₂₂ alkyl halide, in particular iodide, or dialkylsulfate; for obtaining, e.g., a compound of formula (I) wherein R is a group

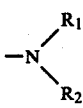

wherein at least one of R₁ and R₂ is methyl or ethyl, suitable alkylating agents are, for instance, methyliodide, dimethylsulfate or, respectively, ethyliodide or diethylsulfate.

Reaction conditions well known to the skilled in the art and well described in the organic chemistry may be followed: see e.g. Lucier et al, Org. Synth. 44, 72 (1964).

The acylation of a compound of formula (I) wherein R is a group

wherein R₁ and R₂ are both hydrogen to obtain a corresponding compound of formula (I) wherein R is a group —NHCOR₃ or —NHSO₂R₄ may be performed, as already said, using an appropriate acylating agent carrying the desired —COR₃ or, respectively, —SO₂R₄ moiety.

Thus, for example, in order to obtain a compound of formula (I) wherein R is a group —NHCOR₃ wherein R₃ is as defined above under (c) a suitable acylating agent may be a carboxylic acid of formula R₃—COOH, wherein R₃ is as hereinbefore indicated, or, preferably, a reactive derivative thereof such as, for instance, an halide, in particular the chloride, or the anhydride or a mixed anhydride thereof.

Similar acylating agents may be used for obtaining compounds of formula (I) wherein R is a group —NHCOR$_3$ wherein R$_3$ is as defined under (a), (b) and (d): for example an oxalohalide, e.g. chloride, may be useful to prepare a compound of formula (I) wherein R is a group —NHCOR$_3$ wherein R$_3$ is carboxy; a C$_1$-C$_3$ alkyl-chloro-carbonate may be used for obtaining a compound of formula (I) wherein R is a group —NHCOR$_3$ wherein R$_3$ is C$_1$-C$_3$ alkoxy; and an halide, e.g. the chloride, of the carbamic acid or its alkylated derivatives may be used for preparing a compound of formula (I) wherein R is a group —NHCOR$_3$ wherein R$_3$ is

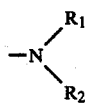

wherein R$_1$ and R$_2$ are as defined above.

Suitable acylating agent for obtaining a compound of formula (I) wherein R is a group —NHSO$_2$R$_4$ may be, e.g., the appropriate sulfonic acid of formula R$_4$SO$_3$H or, preferably, a derivative thereof such as, for instance, a corresponding sulfonyl halide, e.g. chloride, or anhydride.

When the acylation reaction proceeds through elimination of an acid component, the presence of a base, preferably an organic base such as, e.g., triethylamine or pyridine, is generally required; when the base is pyridine, this may also function as solvent, otherwise any appropriate inert, preferably anhydrous, solvent may be employed such as, e.g., toluene, benzene, dioxane, tetrahydrofurane, N,N-dimethylformamide or dimethylsulfoxide. The reaction temperature may vary, e.g., between about 0° C. and about 100° C. and the reaction times may be, e.g., from about one hour to about 48 hours.

Conventional methods may be used for salifying a compound of formula (I) and for obtaining a free compound of formula (I) from a salt thereof, and standard procedures, such as, e.g., fractional crystallization and chromatography, may be followed as well for separating a mixture of isomers of formula (I) into the single isomers.

A compound of formula (II) wherein L is halogen may be prepared halogenating a compound of formula (IV)

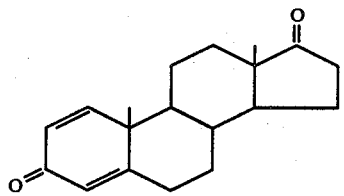

according to known methods, for example by treatment with a N-halosuccinimide or acetamide, e.g. N-bromosuccinimide or N-bromoacetamide, in a halogenated organic solvent such as, e.g., carbon tetrachloride, in accordance with the procedure described by Djerassi et al in J. Am. Chem. Soc. 72, 4531 (1950).

The compounds of formula (II) wherein L is the residue of a reactive ester of an alcohol as defined above are known compounds or may be prepared by known methods from known compounds.

Also the compounds of formula (III) are known compounds which are either commercially available products or compounds which may be prepared by known methods. The compounds of the invention possess high aromatase inhibiting activity.

Aromatase (estrogen synthetase) is the enzyme responsible for the final step in biosynthesis of estrogens; as is known, the conversion of androgens to estrogens (e.g. of androstendione and testosterone to estrone and estradiol) is mediated by aromatase, a microsomal P450 enzyme that acts on the androgenic substrate. The product of aromatase action, i.e. estrogens, besides being essential for reproduction, may also be responsible of the growth of hormone-dependent tumors.

In view of the above, the aromatase inhibitors compounds of the invention may find use for the treatment of the advanced hormone-dependent tumors, in particular, e.g., breast, ovarian, uterine and pancreatic tumors. Owing to their aromatase-inhibiting properties, the compounds of the invention can find application also in the treatment of prostatic hyperplasia, which involves a benign enlargement of the prostatic gland.

Furthermore, the compounds of the invention produce a decrease in estradiol formation and so may be useful for the treatment of male fertility disturbances (Drugs 28: 263, 1984).

Aromatase inhibition by the compounds of the present invention was determined both in vitro (human placental aromatase), and in vivo (ovarian aromatase activity) in rats.

The compounds of the invention were found to be particularly potent, especially in vivo, aromatase inhibitors. Aromatase inhibition in vitro was determined as follows: the enzyme system was isolated from the microsomal fraction of human placental tissue according to standard procedure. The assay of Thompson and Siiteri [E. A. Thompson and P. K. Siiteri, J. Biol. Chem. 249, 5364, 1974] which determines the rate of aromatization as measured by the liberation of $^3$H$_2$O from 4-[1$\beta$,2$\beta$-$^3$H]androstene-3,17-dione was used. All incubations were carried out in a shaking water bath at 37° C. in air in 10 mM potassium phosphate buffer, pH 7.5, which contained 100 mM KCl, 1 mM EDTA and 1 mM dithiothreitol. The experiments were carried out in 1 ml incubation volume containing 50 nM 4-[$^3$H]androstenedione, various concentrations of the inhibitors, 100 $\mu$M NADPH and 0.05 mg of microsomal proteins. After 15 minutes of incubation the reaction was stopped by the addition of chloroform (5 ml). After centrifugation at 1500×g for 5 minutes, aliquots (0.5 ml) were removed from the water phase for determination of $^3$H$_2$O formed. The concentration of each compound required to reduce control aromatase by 50% (IC$_{50}$) was determined by plotting % inhibition versus log of inhibitor concentration. the relative potency of each compound versus 4 OH-A was calculated according to the relation:

$$\text{Relative potency} = \frac{\text{IC}_{50} \text{ of 4 OH—A}}{\text{IC}_{50} \text{ of test compound}}$$

Aromatase inhibition in vivo was determined in rats by the following procedure:

adult female rats were twice treated subcutaneously with 100 I.U. pregnant mares' serum gonadotropin (PMSG) at 4 days' interval, in order to increase ovarian aromatase activity, according to Brodie procedure [A. M. H. Brodie et al, Steroids 38, 693, 1981]. Three days after the second PMSG treatment, groups of 6 animals each were given orally the vehicle (0.5% methocel) or the inhibitor at the dose reported in the following table. Animals were killed 24 hours later, microsomes were isolated from ovaries and their aromatase activity determined using a method similar to that described above for the evaluation of the in vitro activity. The incubation were carried out for 30 minutes in 1 ml incubation volume containing 0.1 mg of microsomal proteins, 100 nM 4-[$^3$H]androstenedione and 100 μM NADPH.

% inhibition of control aromatase activity was calculated. Even if in vitro the compounds of the invention may be only equipotent or less potent than the reference compounds, nevertheless they are more potent aromatase inhibitors in vivo.

The following table reports, e.g., the in vivo activity of the compounds of the invention 6α-azido androsta-1,4-diene-3,17-dione (internal code FCE 24403) and 6α-aminoandrosta-1,4-diene-3,17-dione (internal code FCE 24968) in comparison to that of the well-known aromatase inhibitors 4-hydroxyandrosta-4-ene-3,17-dione (4-OH-A) [A. M. H. Brodie, Cancer Research (Suppl.) 42, 3312 s, 1982], D-homo-17a-oxaandrosta-1,4-diene-3,17-dione (testolactone) [A. M. H. Brodie, Cancer Research (Suppl.) 42, 3312s, 1982 and D. F. Covey and W. F. Hood, Cancer Research (Suppl.) 42, 3327s, 1982], and androsta-1,4-diene-3,17-dione [D. F. Covey and W. F. Hood, Cancer Research (Suppl.) 42, 3327s, 1982].

TABLE

Inhibition of rat ovarian aromatase in vivo.

| Compound | DOSE mg/kg p.o. | % AROMATASE INHIBITION |
| --- | --- | --- |
| 4-hydroxy androsta-4-ene-3,17-dione (4-OH—A) | 100 | 21 N.S. |
|  | 30 | 7 N.S. |
| D-homo-17a-oxaandrosta-1,4-diene-3,17-dione (testolactone) | 30 | 2 N.S. |
| androsta-1,4-diene-3,17-dione | 30 | 37* |
| 6α-azido androsta-1,4-diene-3,17-dione (FCE 24403) | 30 | 89** |
|  | 10 | 81** |
| 6α-aminoandrosta + 1,4-diene-3,17-dione (FCE 24968) | 30 | 71** |
|  | 10 | 53** |

N.S. = not significant; *p < 0.05; **p < 0.01 versus vehicle treated group

Although the compounds FCE 24403 and FCE 24968 are less potent in vitro than, e.g., 4-OH-A, they are very effective when administered in vivo by oral route at, e.g., 10 mg/kg, as a consequence of an unusual resistance to hepatic metabolization, while 4-OH-A is ineffective even at a dose 10 times higher (100 mg/kg).

The major disadvantage for therapeutical use of 4-OH-A as antitumor agents in women is the need of parenteral administration, the compound being extensively conjugated after oral administration [R. C. Coombes et al., Lancet II, 1237, 1984].

The new class or aromatase inhibitors here described offers a good improvement for the oral therapy of estrogen dependent diseases, such as pre- and post-menopausal breast tumor, ovarian tumor, uterine tumor, pancreatic tumor, prostatic hyperplasia and other estrogen related diseases.

The compounds of the invention can be administered in a variety of dosage forms, e.g. orally, in the form of tablets, capsules, sugar or film coated tablets, liquid solutions or suspensions; rectally, in the form of suppositories; parenterally, e.g. intramuscularly, or by intravenous injection or infusion, or topically.

The dosage depends on the age, weight, conditions of the patient and administration route; for example the dosage adopted for oral administration to adult humans may range from about 10 to about 200 mg pro dose, from 1 to 5 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluent, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations.

Said pharmaceutical preparations may be manufactured in known manner, for example, by means of mixing, granulating, tabletting, sugar-coating, or filml-coating processes. The liquid dispersions for oral administration may be e.g. syrups, emulsions and suspensions.

The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

Compositions for topical application such as, e.g. creams, lotions or pastes, may be, e.g. prepared by admixing the active ingredient, with a conventional oleaginous or emulsifying excipient.

The following examples illustrate but do not limit the invention.

EXAMPLE 1

A solution of 10 g of androsta-1,4-diene-3,17-dione in 95 ml of carbon tetrachloride is refluxed with 6.4 g of N-bromosuccinimide and 0.4 g of benzoyl peroxide for seventy five minutes. After filtration of succinimide, the filtrate was cooled in ice until crystallization is complete. The mixture is then filtered and dried so obtaining 9.8 g of crude 6-bromoandrosta-1,4-diene-3,17-dione satisfactory for the next step. The analytical sample is crystallized from diethyl ether/n-hexane, m.p. 188°–190° C., $[\alpha]_D^{20°}+116$, U.V. (95% EtOH) $\lambda$max=250 nm.

EXAMPLE 2

To a solution of 6$\beta$-bromoandrosta-1,4-diene-3,17-dione (5.0 g) in 250 ml of dimethylformamide, 1,15 g of powdered sodium azide dissolved in 14 ml of water are added and the mixture is warmed to 100° C. and maintained with stirring at the same temperature for 120 minutes. The entire mixture is then poured into 1 l of water and extracted with four 200 ml portions of ethyl acetate. The combined extracts are washed with saturated aqueous sodium chloride solution and dried. The solvent is then removed in vacuum to yield a crude product which is purified by chromatography on Al$_2$O$_3$ (neutral activity) with ethyl acetate:n-hexane 40:60 as eluant so obtaining 3.4 g of pure 6$\alpha$-azido androsta-1,4-diene-3,17-dione. The analytical sample was crystallized from methanol, m.p. 168°–170° C.; $[\alpha]_D^{20°}+93.2°$ (c=1, CHCl$_3$); U.V. (95% EtOH) $\lambda$max=244; $\epsilon$=17,420; N.M.R. (CDCl$_3$) $\delta$: 0.98 (3H, s); 1.3 (3H, s); 4.31 (1H, ddd); 6.44 (1H, dd); 6.26 (1H, dd); 7.02 (1H, d). Following analogous procedure the 6$\beta$-azido androsta-1,4-diene-3,17-dione can be prepared, starting from 6$\alpha$-bromo androsta-1,4-diene-3,17-dione.

EXAMPLE 3

To a solution of 6$\beta$-methanesulfonyloxy androsta-1,4-diene-3,17-dione (3.0 g) in 150 ml of dimethylformamide, 0.67 g of sodium azide dissolved in 8.5 ml of water are added and the mixture is warmed to 100° C. and maintained with stirring at the same temperature for 90 minutes.

With external cooling the entire mixture is poured into 600 ml of water and extracted with four 150 ml portions of ethyl acetate. The combined extracts are washed with saturated sodium chloride solution in order to remove any residual dimethylformamide and dried over anhydrous sodium sulphate. The solvent is then removed in vacuum to yield a crude product which is purified by chromatography on Al$_2$O$_3$ (neutral activity) with ethyl acetate:n-hexane 40:60 as eluant so obtaining 1.95 g of pure 6$\alpha$-azido androsta-1,4-diene-3,17-dione, m.p. 167°–169° C.; $[\alpha]_D+92.8°$ (c=1, CHCl$_3$).

In analogous fashion 6 ($\alpha$, $\beta$)-azido androsta-1,4-diene-3,17-dione can be obtained.

EXAMPLE 4

To a stirred solution of 6$\alpha$-azidoandrosta-1,4-diene-3,17-dione (0.61 g) in tetrahydrofuran (3 ml) is added triphenylphosphine (0.79 g).

After the evolution of nitrogen has ceased, the reaction mixture is diluted with water (1 ml) and refluxed for 24 hrs.

The cooled reaction mixture is poured into 1N HCl aqueous solution (50 ml) and washed with methylene chloride.

The aqueus layer is brought to pH 10 by adding a NaOH aqueous solution and thoroughly extracted with methylene chloride. The organic phase is dried on CaCl$_2$ and evaporated in vacuo to yield a yellow foam (0.44 g) which is taken up with diethyl ether (30 ml) and treated with gaseous HCl.

The resulting precipitate is filtered off, dried and partitioned between methylene chloride and a 2N NaOH aqueous solution.

The organic layer is separated, dried on CaCl$_2$, and evaporated in vacuo to yield 6$\alpha$-aminoandrosta-1,4-diene-3,17-dione (0.40 g), m.p. 186°–191° C.;
N.M.R. (CDCl$_3$) $\delta$: 0.93 (3H, s); 1.25 (3H, s); 3.71 (1H, ddd); 6.26 (1H, dd); 6.39 (1H, dd): 7.01 (1H, d).
I.R. (KBr) cm$^{-1}$: 3450, 3380, 3000, 2940, 2860, 1730, 1655, 1615, 1600.

In analogous fashion the 6$\beta$-amino androsta-1,4-diene-3,17-dione can be prepared, and also 6($\alpha$, $\beta$)-amino androsta-1,4-diene-3,17-dione.

EXAMPLE 5

To a stirred solution of 6$\alpha$-amino androsta-1,4-diene-3,17-dione (1,4 g) in 5.5 ml of dry pyridine, 2.8 ml of acetic anhydride are added dropwise at room temperature. The solution is stirred for 90 minutes and then water is dropped into the cooled (0° C.) solution. After 10 minutes stirring the reaction mixture is extracted with five 100 ml portions of ethyl acetate which are collected and dried over anhydrous sodium sulphate. The solvent is then removed in vacuum to yield a crude which is purified by chromatography on silica gel so obtaining 1.30 g of pure 6$\alpha$-acetylamino androsta-1,4-diene-3,17-dione;
N.M.R. (CDCl$_3$) $\delta$: 2.03 (3H, s); 4.20 (1H, m); 6.25 (1H, dd); 6.45 (1H, ddd); 6.50 (1H, m); 7.01 (1H, dd).

Following analogous procedure, using the appropriate anhydride or acylchloride, the following 6-acylamino derivatives can be prepared:
6$\alpha$-propionylamino androsta-1,4-diene-3,17-dione;
6$\alpha$-hexanoylamino androsta-1,4-diene-3,17-dione;
6$\alpha$-octanoylamino androsta-1,4-diene-3,17-dione;
6$\alpha$-decanoylamino androsta-1,4-diene-3,17-dione;
6$\alpha$-dodecanoylamino androsta-1,4-diene-3,17-dione;
6$\alpha$-octadecanoylamino androsta-1,4-diene-3,17-dione;
6$\alpha$-pivaloylamino androsta-1,4-diene-3,17-dione;
6$\alpha$-monomalonylamino androsta-1,4-diene-3,17-dione;
6$\alpha$-monosuccinylamino androsta-1,4-diene-3,17-dione;
6$\alpha$-formylamino androsta-1,4-diene-3,17-dione;
6$\alpha$-oxaloamino androsta-1,4-diene-3,17-dione;
6$\beta$-acetylamino androsta-1,4-diene-3,17-dione;
6$\beta$-propionylamino androsta-1,4-diene-3,17-dione;
6$\beta$-hexanoylamino androsta-1,4-diene-3,17-dione;
6$\beta$-octanoylamino androsta-1,4-diene-3,17-dione;
6$\beta$-decanoylamino androsta-1,4-diene-3,17-dione;
6$\beta$-dodecanoylamino androsta-1,4-diene-3,17-dione;
6$\beta$-octadecanoylamino androsta-1,4-diene-3,17-dione;
6$\beta$-pivaloylamino androsta-1,4-diene-3,17-dione;
6$\beta$-monomalonylamino androsta-1,4-diene-3,17-dione;
6$\beta$-monosuccinylamino androsta-1,4-diene-3,17-dione;
6$\beta$-formylamino androsta-1,4-diene-3,17-dione;
6$\beta$-oxaloamino androsta-1,4-diene-3,17-dione,
and the 6($\alpha$, $\beta$) mixtures of all the compounds mentioned above.

EXAMPLE 6

To a stirred and cooled (0° C.) solution of 6$\alpha$-amino androsta-1,4-diene-3,17-dione (1.2 g) in CH$_2$Cl$_2$ (20 ml), triethylamine (1.1 ml) and dimethylcarbamoylchloride (0.6 ml) are added dropwise. A catalytic amount of 4-dimethylaminopyridine is added too and the mixture is maintained at 0° C. for three hours and then allowed to rise to room temperature. The reaction mixture is diluted with ethyl acetate, washed some times with water and then with a saturated sodium chloride solution. The organic phase is dried over anhydrous sodium sulphate and the solvent is removed in vacuum to give a crude which is purified by flash chromatography so obtaining 1.05 g of pure 6α-(N',N'-dimethylcarbamido)-androsta-1,4-diene-3,17-dione;

N.M.R. (CDCl$_3$) δ: 2.95 (6H, s); 4.22 (1H, m); 6.26 (1H, dd); 6.43 (1H, ddd); 6.48 (1H, m); 7.02 (1H, d).

Following the same method using diethylcarbamoyl chloride the corresponding 6α-(N',N'-diethylcarbamido)-androsta-1,4-diene-3,17-dione is obtained.

By analogous procedure the following compounds can be prepared:
6α-ethoxycarbonylamino androsta-1,4-diene-3,17-dione;
6α-methanesulfonylamino androsta-1,4-diene-3,17-dione;
6α-(p-toluenesulfonyl)-amino androsta-1,4-diene-3,17-dione;
6β-ethoxycarbonylamino androsta-1,4-diene-3,17-dione;
6β-methanesulfonylamino androsta-1,4-diene-3,17-dione;
6β-(p-toluenesulfonyl)-amino androsta-1,4-diene-3,17-dione,
and the 6(α, β) mixtures of all the compounds mentioned above.

EXAMPLE 7

In a dry flask, flushed with nitrogen, xylene (10 ml) and thriethylborane (10 mmol) are charged. The stirred solution is heated to reflux and then 6α-azido androsta-1,4-diene-3,17-dione (3.0 g) is added.

After evolution of nitrogen is ceased the solution is cooled, 30 ml of diethyl ether are added and the amine is extracted with 6N aqueous hydrochloric acid.

The aqueous phase is washed with diethyl ether. The solution is then made alkaline with sodium hydroxide and the amine is extracted with four 200 ml portions of ethyl acetate which are collected and dried over anhydrous sodium sulphate. The solvent is removed in vacuum to yield a crude which is purified by flash chromatography so obtaining 2.45 g of pure 6α-ethylamino androsta-1,4-diene-3,17-dione;

N.M.R. (CDCl$_3$) δ: 1.02 (3H, d); 2.54 (2H, m); 3.65 (1H, m); 6.27 (1H, dd); 6.40 (1H, ddd); 7.03 (1H, d).

Following analogous procedure the following compounds can be prepared:
6α-methylamino androsta-1,4-diene-3,17-dione;
6β-methylamino androsta-1,4-diene-3,17-dione;
6β-ethylamino androsta-1,4-diene-3,17-dione;
6α-propylamino androsta-1,4-diene-3,17-dione; and
6β-propylamino androsta-1,4-diene-3,17-dione.

EXAMPLE 8

A solution of 0.65 g of 6α-amino androsta-1,4-diene-3,17-dione in 30 ml of ethanol is treated with 21.71 ml of 0.1N HCl aqueous solution. The yellow solution is discoloured, then it is filtered and the alcohol is removed at reduced pressure. The resulting aqueous solution is lyophilized to give 0.7 g of dry 6α-amino androsta-1,4-diene-3,17-dione hydrochloride as slight yellow powder. By analogous procedure the hydrochlorides of the 6-amino derivatives prepared according to the examples 4, 7 and 9 are prepared.

Similarly the salts with sulfuric, phosphoric, citric, fumaric, succinic, malic and tartaric acid can be prepared for all the compounds mentioned in the same examples 4, 7 and 9.

EXAMPLE 9

Into a vessel cooled to 5° C. with an external ice bath benzaldehyde (0.166 g) and 6α-amino androsta-1,4-diene-3,17-dione (0.299 g) are dissolved in 30 ml of dry benzene; the mixture is then stirred for 2 hours at room temperature, the solvent is removed by distillation and the crude residue is purified by crystallization from ethylacetate/n-hexane. The N-benzylidene-6α-amino androsta-1,4-diene-3,17-dione is heated with 0.156 g of methyliodide in a pressure bomb at 100° C. for 24 hours and the dark oil is quenched in 50 ml of ice and water. The resulting mixture is washed with diethyl ether and the aqueous phase is then heated at 100° C. for 20 minutes, 0.10 g of sodium hydroxide is added and the warming is continued with stirring for 2 hours.

The mixture is cooled, extracted with ethyl acetate, the solvent is removed in vacuum and the residue is purified by chromatography to yield 0.15 g of pure 6α-methylamino androsta-1,4-diene-3,17-dione.

In analogous way 6β-methyl aminoandrosta-1,4-diene-3,17-dione and 6(α, β)-methyl aminoandrosta-1,4-diene-3,17-dione can be obtained.

EXAMPLE 10

Tablets each weighing 0.150 g and containing 25 mg of the active substance, can be manufactured as follows:
Composition (for 10,000 tablets)

| | |
|---|---|
| 6α-azido androsta-1,4-diene-3,17-dione | 250 g |
| Lactose | 800 g |
| Corn starch | 415 g |
| Talc powder | 30 g |
| Magnesium stearate | 5 g |

The 6α-azido androsta-1,4-diene-3,17-dione, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate is added, carefully mixed and processed into tablets.

EXAMPLE 11

Capsules, each dosed at 0.200 g and containing 20 mg of the active substance can be prepared as follows:
Composition for 500 capsules:

| | |
|---|---|
| 6α-amino androsta-1,4-diene-3,17-dione | 10 g |
| Lactose | 80 g |
| Corn starch | 5 g |
| Magnesium stearate | 5 g |

This formulation can be encapsulated in two-piece hard gelatin capsules and dosed at 0.200 g for each capsule.

EXAMPLE 12

Intramuscular Injection 25 mg/ml
An injectable pharmaceutical composition can be manufactured by dissolving 25 g of 6α-azido androsta-1,4-diene-3,17-dione in sterile propyleneglycol (1000 ml) and sealing ampoules of 1-5 ml.

We claim:

1. A compound of formula (I)

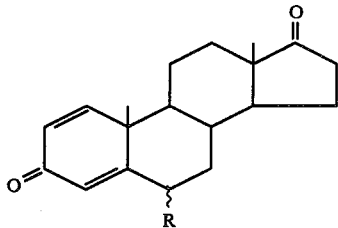

wherein
R is
(1) the group —N₃;
(2) a group

wherein each of $R_1$ and $R_2$ is, independently, hydrogen or unsubstituted $C_1$-$C_{22}$ alkyl;
(3) a group —NHCOR₃ wherein $R_3$ is
  (a) hydrogen;
  (b) $C_1$-$C_3$ alkoxy or carboxy;
  (c) $C_1$-$C_{22}$ alkyl either unsubstituted or substituted by a carboxy group; or
  (d) a group

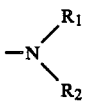

wherein $R_1$ and $R_2$ are as defined above; or
(4) a group —NHSO₂R₄ wherein $R_4$ is unsubstituted $C_1$-$C_4$ alkyl, or phenyl either unsubstituted or substituted by $C_1$-$C_3$ alkyl, halogen or nitro,
and the pharmaceutically acceptable salts thereof.

2. A compound of formula (I) according to claim 1, wherein R is
(1) —N₃;
(2) a group

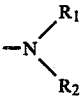

wherein each of $R_1$ and $R_2$ is, independently, hydrogen or $C_1$-$C_4$ alkyl;
(3) a group —NHCOR₃, wherein $R_3$ is (a') hydrogen; (b') $C_1$-$C_3$ alkoxy or carboxy; (c') unsubstituted $C_1$-$C_{17}$ alkyl or $C_1$-$C_4$ alkyl substituted by carboxy; or
(4) a group —NHSO₂R₄, wherein $R_4$ is unsubstituted $C_1$-$C_4$ alkyl, or phenyl either unsubstituted or substituted by $C_1$-$C_3$ alkyl,
and the pharmaceutically acceptable salts thereof.

3. A process for preparing a compound of formula (I) according to claim 1, or a pharmaceutically acceptable salt thereof, the process comprising:
(A) reacting a compound of formula (II)

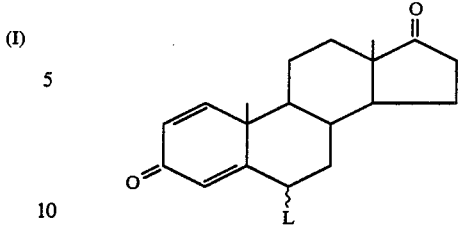

wherein
L is a leaving group displaceable by nucleophilic substitution, with a compound of formula (III)

M—N₃   (III)

wherein
M is an alkali metal or ammonium cation or a trialkylsilyl group, so obtaining a compound of formula (I) wherein R is the group —N₃; or
(B) reducing a compound of formula (I) wherein R is the group —N₃ so obtaining a compound of formula (I) wherein R is a group

wherein, depending upon the reaction conditions, $R_1$ and $R_2$ are both hydrogen or one of $R_1$ and $R_2$ is hydrogen and the other is unsubstituted $C_1$-$C_{22}$ alkyl; or
(C) alkylating a compound of formula (I) wherein R is a group

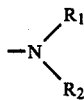

wherein $R_1$ and $R_2$ are both hydrogen, so obtaining a compound of formula (I) wherein at least one of $R_1$ and $R_2$ is unsubstituted $C_1$-$C_{22}$ alkyl; or
(D) acylating a compound of formula (I) wherein R is a group

wherein $R_1$ and $R_2$ are both hydrogen, with an acylating agent carrying a —COR₃ or SO₂R₄ moiety, wherein $R_3$ and $R_4$ are as defined in claim 1, so obtaining a compound of formula (I) wherein R is a group —NHCOR₃ or, respectively, a group —NHSO₂R₄, wherein $R_3$ and $R_4$ are as defined in claim 1; and, if desired, salifying a compound of formula (I) or obtaining a free compound of formula (I) from a salt thereof and/or, if desired, separating a mixture of isomers of formula (I) into the single isomers.

4. A method of producing an aromatase inhibiting effect comprising administering to a patient in need of such effect an effective amount of the compound of claim 1.

5. A method of inhibiting hormone-dependent tumors comprising administering to a patient in need of such inhibition an effective amount of the compound of claim 1.

6. A pharmaceutical composition for producing an aromatase inhibiting effect or for inhibiting hormone-dependent tumors, said composition containing an effective amount of a compound of claim 1 as the active principle, and a pharmaceutically acceptable carrier and/or diluent therefor.

7. A method of producing an aromatase inhibiting effect comprising administering to a patient in need of such effect an effective amount of the composition of claim 6.

8. A method of inhibiting hormone-dependent tumors comprising administering to a patient in need of such inhibition an effective amount of a composition of claim 6.

9. A compound, in the form of a 6α- or 6β-epimer or 6(α, β)-epimeric mixture, chosen from the group consisting of:
6-azido androsta-1,4-diene-3,17-dione;
6-amino androsta-1,4-diene-3,17-dione;
6-methylamino androsta-1,4-diene-3,17-dione;
6-(N',N'-dimethylcarbamido)-androsta-1,4-diene-3,17-dione;
6-ethylamino androsta-1,4-diene-3,17-dione;
6-(N',N'-diethylcarbamido)-androsta-1,4-diene-3,17-dione;
6-formylamino androsta-1,4-diene-3,17-dione;
6-ethoxycarbonylamino androsta-1,4-diene-3,17-dione;
6-oxaloamino androsta-1,4-diene-3,17-dione;
6-acetylamino androsta-1,4-diene-3,17-dione;
6-propionylamino androsta-1,4-diene-3,17-dione;
6-methanesulfonylamino androsta-1,4-diene-3,17-dione;
6-(p-toluenesulfonyl)amino androsta-1,4-diene-3,17-dione,
and the pharmaceutically acceptable salts of the compounds containing a salifiable group.

* * * * *